United States Patent
Wong

(10) Patent No.: US 7,906,093 B2
(45) Date of Patent: Mar. 15, 2011

(54) METHOD OF SYNTHESIZING ZIRCONIUM PHOSPHATE PARTICLES

(75) Inventor: Raymond J. Wong, Norman, OK (US)

(73) Assignee: Renal Solutions, Inc., West Lafayette, IN (US)

( * ) Notice: Subject to any disclaimer, the term of this patent is extended or adjusted under 35 U.S.C. 154(b) by 0 days.

(21) Appl. No.: 12/772,468

(22) Filed: May 3, 2010

(65) Prior Publication Data

US 2010/0213412 A1    Aug. 26, 2010

Related U.S. Application Data

(62) Division of application No. 12/431,998, filed on Apr. 29, 2009, now Pat. No. 7,736,507, which is a division of application No. 11/302,757, filed on Dec. 14, 2005, now Pat. No. 7,566,432.

(60) Provisional application No. 60/639,740, filed on Dec. 28, 2004.

(51) Int. Cl.
    *C01B 25/37*    (2006.01)
(52) U.S. Cl. .......................... 423/308; 423/309; 423/311
(58) Field of Classification Search .................. 423/308, 423/309, 311
    See application file for complete search history.

(56) References Cited

U.S. PATENT DOCUMENTS

| | | | |
|---|---|---|---|
| 3,416,884 A | 12/1968 | Stynes et al. | |
| 4,381,289 A | 4/1983 | Nowell et al. | |
| 4,629,656 A | 12/1986 | Alberti et al. | |
| 4,826,663 A | 5/1989 | Alberti et al. | |
| 5,387,724 A | 2/1995 | Johnstone et al. | |
| 5,441,717 A | 8/1995 | Ohsumi et al. | |
| 6,627,164 B1 | 9/2003 | Wong | |
| 6,818,196 B2 | 11/2004 | Wong | |
| 6,936,175 B2 | 8/2005 | Bortun et al. | |
| 7,385,803 B2 | 6/2008 | Alberti et al. | |
| 7,566,432 B2 | 7/2009 | Wong | |
| 2002/0112609 A1 | 8/2002 | Wong | |
| 2003/0103888 A1 | 6/2003 | Hai et al. | |
| 2009/0208399 A1 | 8/2009 | Wong | |

FOREIGN PATENT DOCUMENTS

| | | |
|---|---|---|
| GB | 1007871 | 10/1965 |
| GB | 1476641 | 6/1977 |
| JP | 59069428 A | 4/1984 |
| JP | 62226807 A | 10/1987 |

OTHER PUBLICATIONS

Cobe Renal Care, Inc., "Guide to Custom Dialysis," Product No. 306100-005, Revision E, Sep. 1993, pp. 1-54.
Cobe Renal Care, Inc., "Sorbent Dialysis Primer," Production No. 306100-006, Edition 4, Sep. 1993, pp. 1-51.
International Search Report and Written Opinion for Internetional Patent Application No. PCT/US2005/045252 dated Apr. 24, 2006.
Jiménez-Jiménez et al., "Surfactant-Assisted Synthesis of a Mesoporous Form of Zircomium Phosphate with Acidic Properties," Advanced Materials, vol. 10, No. 10, 1998, pp. 812-815.
Pacheco et al., "Syntheses of Mesoporous Zirconia with Anionic Surfactants," J. Mater. Chem., vol. 8, No. 1, 1998, pp. 219-226.
Bogdanov et al., "Structure of Zirconium Phosphate Gels Produced by the Sol-Gel Method," Journal of Physics: Condensed Matter, vol. 9, 1997, pp. 4031-4039, (abstract only).
Ferrangina et al., "Synthesis and Characterization of Sol-Gel Zirconium Phosphate with Template Surfactants by Different Methods," Journal of Thermal Analysis and Calorimetry, vol. 71, No. 3, 2003, pp. 1023-1033, (abstract only).
Sharygin et al., "Sol-Gel Technique for Production of Spherically Granulated Zirconium(IV) Phophate," Russian Journal of Applied Chemistry, vol. 78, No. 2, 2005, pp. 229-234, (abstract only).
Jignasa et al., "A Study on Equilibrium and Kinetics of Ion Exchange of Alkaline Earth Metals Using an Inorganic Cation Exchanger—Zirconium Titanium Phosphate," Journal of Chemical Science, vol. 118, No. 2, Mar. 2006, pp. 185-189.
Sun, Zhengfei, "Novel Sol-Gel Nanoporous Materials, Nanocomposites and Their Applications in Bioscience," Drexel University, Sep. 2005, pp. 27-62.
Ferragina et al., "Synthesis and Characterization of Sol-Gel Zirconium Phosphate with Template Surfactant", CNR, IMAI-ICMAT, via Salaria Km. 29.300, 00016, (year unknown), (abstract only).

*Primary Examiner* — Wayne Langel
(74) *Attorney, Agent, or Firm* — Kilyk & Bowersox, P.L.L.C.

(57) ABSTRACT

Zirconium phosphate particles are synthesized by providing a solution of zirconium oxychloride in an aqueous solvent, adding at least one oxygen-containing additive to the solution, the oxygen-containing additive being selected to form a complex with zirconium ions in the solution of zirconium oxychloride and thereby reduce hydration of the zirconium ions, and combining this solution with phosphoric acid or a phosphoric acid salt to obtain zirconium phosphate particles by sol gel precipitation.

25 Claims, No Drawings

METHOD OF SYNTHESIZING ZIRCONIUM PHOSPHATE PARTICLES

This application is a divisional of U.S. patent application Ser. No. 12/431,998, filed Apr. 29, 2009 (now allowed), which in turn is a divisional of U.S. patent application Ser. No. 11/302,757, filed Dec. 14, 2005 (now U.S. Pat. No. 7,566,432 B2), which in turn claims priority under 35 U.S.C. §119(e) of prior U.S. Provisional Patent Application No. 60/639,740 filed Dec. 28, 2004, which is incorporated in its entirety by reference herein.

FIELD OF INVENTION

The present invention relates to zirconium phosphate particles and in particular, to methods of making zirconium phosphate particles, such as by sol gel synthesis.

BACKGROUND OF THE INVENTION

Zirconium phosphate (ZrP) particles are used as ion exchange materials and are particularly useful as a sorbent material for regenerative dialysis. Zirconium phosphate (ZrP) particles can be synthesized by a sol gel process using zirconium oxychloride (ZOC), also called zirconyl chloride, as a starting material. ZOC is a preferred starting material because it is abundant and commercially available at a low price.

Sol gel precipitation, as the term is used herein, refers generally to a process for forming a ceramic or catalyst in which colloidal particles (called sol) are formed by reacting hydrated metal ions (group III and IV) with a precipitating agent, followed by the polymerization of the colloidal particles to form gel particles. See, for example, Bogdanov S G et al., Structure of zirconium phosphate gels produced by the sol-gel method, J. Phys.: Condens. Matter 9 4031-4039 (1997), incorporated herein by reference. Sol gel precipitation is a particularly advantageous method of obtaining zirconium phosphate from zirconium oxychloride since it is a direct, single-step conversion process that can be carried out at room temperature. Hence, it offers great advantages in efficiency and manufacturing costs in comparison with other processes. Moreover, zirconium phosphate particles obtained by sol gel precipitation generally have a high porosity and a high BET surface area, which enhances their adsorption capacity for ammonia. Further, the use of the sol gel precipitation method allows for control over particle size and morphology of the product, as well as control over impurity levels. These characteristics for zirconium phosphate particles are important with respect to ammonia adsorption and cartridge design for dialysis applications.

Despite all of these advantages, the sol gel precipitation is not easy to accomplish on a manufacturing scale. The difficulties are mainly caused by the nature of the raw material (e.g., ZOC), the rapid rate of the reaction, which is difficult to control, and the lack of appropriate process control methods (flow rate, agitation rate, concentration, etc.). These difficulties can be described as follows.

Sol gel zirconium phosphate, when precipitated directly from zirconium oxychloride solution using phosphoric acid as a precipitating agent, is in the form of soft gel particles having a wide range of particle sizes. One reason why this happens is that zirconium ions in a solution of zirconium oxychloride are highly hydrated monomers, that is, they are surrounded by a large number of coordinated water molecules. During the formation of zirconium phosphate, the soft gel particles tend to agglomerate when the product slurry gets thicker during the reaction process, or when the particles are packed during the filtration and drying process. As a result of this agglomeration, large aggregates are present in the end product after drying so that milling or grinding is required to obtain a free-flowing powder, with the further disadvantage that milling produces a lot of excessively fine particles. Agglomeration also increases the particle size to an extent that is undesirable for column or separation applications.

A wide range of particle sizes in the finished product is a common result of the conventional sol gel precipitation process for the additional reason that the particle size depends on the concentration of the reactants, which gradually decreases as precipitation continues, causing the formation of smaller particles. Thus, it is difficult to control particle size using a single reactant addition technique. Large particles and excessively fine particles are both undesirable for dialysis application because large particles can cause ammonia leakage and smaller adsorption capacity, while fine particles can increase flow resistance and pressure drop in a sorbent cartridge.

Further, the agglomeration of sol gel zirconium phosphate during the precipitation process interferes with agitation and mixing of the reactants as the slurry concentration increases, resulting in the formation of an excessive number of fine particles.

The particle size of sol gel zirconium phosphate can be increased by increasing the amount and concentration of phosphoric acid (for example, by providing a ratio of $ZrO_2$:$PO_4$ of 1:3) but the increase in phosphoric acid also enhances the gelation effect as excess lattice $H^+$ in ZrP combines with $H_2O$ molecules.

Accordingly, there is a need for an improved method of synthesizing zirconium phosphate particles that can be carried out on a manufacturing scale.

There is a further need for an improved method of synthesizing zirconium phosphate particles that overcomes one or more of the above-mentioned disadvantages.

SUMMARY OF THE INVENTION

A feature of the present invention is to provide a method of synthesizing zirconium phosphate particles by a sol gel technique that avoids one or more of the above-mentioned disadvantages.

Another feature of the present invention is to provide a method of synthesizing zirconium phosphate particles by a sol gel technique that avoids the creation of soft gel particles and/or that avoids agglomeration of zirconium phosphate gel particles.

Another feature of the present invention is to provide a method of synthesizing zirconium phosphate particles by a sol gel technique and/or to provide particles having a desirable hardness, particle size, particle size range, shape, packing density, porosity, BET surface area for adsorption, and/or adsorption capacity.

Additional advantages of the present invention will be set forth in part in the description that follows, and in part will be apparent from the description, or may be learned by practice of the present invention. The goals and advantages of the present invention will be realized and attained by means of the elements particularly pointed out in the appended claims.

To achieve the above noted goals and in accordance with the purposes of the present invention, as embodied and broadly described herein, the present invention provides a method for synthesizing zirconium phosphate particles by combining zirconium oxychloride and at least one oxygen-containing additive, preferably in an aqueous solvent, to form a solution wherein the oxygen-containing additive(s) can form a complex with zirconium ions in the solution and thereby reduce hydration of the zirconium ions, and then combining the solution with phosphoric acid or a phosphoric acid salt to obtain zirconium phosphate particles by sol gel precipitation.

The present invention further provides a method of synthesizing zirconium phosphate particles having a controlled particle size or particle size distribution. The method includes reacting zirconium oxychloride with phosphoric acid to obtain zirconium phosphate particles by sol gel precipitation. For instance, the method can include providing a reaction vessel having an agitator and adding a solution of zirconium oxychloride and a solution of phosphoric acid simultaneously to the reaction vessel so that zirconium ions react with the phosphoric acid to obtain zirconium phosphate particles by sol gel precipitation. The particle size and/or particle size distribution of the zirconium phosphate particles obtained are controlled by controlling at least one of the following parameters: the rate at which the solution of zirconium oxychloride is added to the reaction vessel, the rate at which the solution of phosphoric acid is added to the reaction vessel, the pH of the solution of phosphoric acid, the concentration of zirconium oxychloride and phosphoric acid in the reaction vessel, and the speed of the agitator.

The present invention further provides a method of synthesizing zirconium phosphate particles by combining zirconium oxychloride and at least one oxygen-containing additive in an aqueous solvent, to form a solution wherein the oxygen-containing additive(s) can form a complex with zirconium ions in the solution and thereby reduce hydration of the zirconium ions, and then combining the solution with phosphoric acid or a phosphoric acid salt to obtain zirconium phosphate particles by sol gel precipitations. The method can include subjecting an aqueous slurry containing the zirconium phosphate particles to a heat treatment.

The present invention further provides a method of making zirconium phosphate particles comprising adding a solution of zirconium oxychloride and a solution of phosphoric acid simultaneously to a reaction vessel to obtain zirconium phosphate particles by sol gel precipitation.

The present invention further provides a method of making zirconium phosphate particles comprising:

(a) combining at least one fluorine-containing additive with zirconium oxychloride in an aqueous solvent to form a solution wherein the fluorine-containing additive forms a complex with zirconium ions in the solution, and (b) combining the solution obtained in (a) with phosphoric acid or a phosphoric acid salt to obtain zirconium phosphate particles by sol gel precipitation.

The present invention further provides a composition comprising a water-soluble zirconium-containing polymer in an aqueous solution, wherein the polymer is formed by combining, in an aqueous solvent, zirconium oxychloride with at least one oxygen-containing additive that is capable of forming a complex with zirconium ions.

The present invention further provides zirconium phosphate particles comprising the following characteristics: a particle size distribution of less than 20% in the range of >60-120 microns, more than 80% in the range of 30-60 microns, and less than 10% in the range of less than 30 microns, an ammonia capacity of 15-20 mg $NH_4$—N/gm ZP, or more particularly, 16-17 mg $NH_4$—N/gm ZP, and an $Na^+$ content of 3.8-6.2 wt %.

The present invention further provides a dialysis cartridge comprising a cartridge that contains the zirconium phosphate particles comprising the following characteristics: a particle size distribution of less than 20% in the range of >60-120 microns, more than 80% in the range of 30-60 microns, and less than 10% in the range of less than 30 microns, an ammonia capacity of 15-20 mg $NH_4$—N/gm ZP, or more particularly, 16-17 mg $NH_4$—N/gm ZP, and an $Na^+$ content of 3.8-6.2 wt %.

It is to be understood that both the foregoing general description and the following detailed description are exemplary only and are not restrictive of the present invention, as claimed.

DETAILED DESCRIPTION OF THE PRESENT INVENTION

The present invention relates in part to a method of synthesizing zirconium phosphate particles by a sol gel technique using a solution of zirconium oxychloride in which the hydration of zirconium ions in the solution has been reduced. This can be accomplished, for example, by the use of an additive or additives in the zirconium oxychloride solution to change the zirconium ions in the solution from a highly hydrated monomeric form to a soluble polymeric zirconium complex with a high number of polymer units and a reduced water of hydration.

In one embodiment, the present invention relates to a method of making zirconium phosphate particles comprising: (a) combining at least one oxygen-containing additive with zirconium oxychloride in an aqueous solvent to form a solution wherein the oxygen-containing additive forms a complex with zirconium ions in the solution, and (b) combining the solution obtained in (a) with phosphoric acid or a phosphoric acid salt to obtain zirconium phosphate particles by sol gel precipitation. As typical, non-limiting amounts, the at least one oxygen containing additive can be about 0.1 to 20% by weight of the zirconium oxychloride and the molar ratio of zirconium oxychloride to phosphoric acid may be from 1:2.8 to 1:3.2. The aqueous solvent can be deionized water or RO water. The zirconium oxychloride can be dissolved in the aqueous solvent and then the oxygen-containing additive can be added to form the solution of step (a). The zirconium oxychloride can be dissolved in the aqueous solvent and then the oxygen-containing additive can be added to form the solution of step (a). The zirconium oxychloride can be present in the aqueous solvent at a saturation concentration or other concentration levels. The oxygen-containing additive can be dissolved in the aqueous solvent and then the zirconium oxychloride can be added to form the solution of step (a). The oxygen-containing additive can be present in the solution of step (a) in a molar amount sufficient so that all or substantially all of the zirconium ions in the solution are converted to a complex. The oxygen-containing additive can form a soluble polymer with zirconium ions.

To explain how an additive can affect the characteristics of zirconium phosphate formed in a sol gel process, it helps to understand the nature of the zirconium ions in a zirconium oxychloride solution in the absence of an additive. Zirconium ions in a zirconium oxychloride solution by itself are highly hydrated zirconium species with 4-8 molecules of $H_2O$ coordinated with each Zr atom. The hydrated ions may form polymeric units ranging from a monomer, $ZrOOH^+$, to a tetramer, $Zr_4(OH)_8^{+8}$, depending on the concentration of the solution. As phosphoric acid is mixed with a zirconium oxychloride solution at room temperature, a sol gel zirconium phosphate precipitate is formed at a very rapid rate, trapping a large number of coordinated water molecules (or hydronium ions since the lattice $H^+$ can combine with $H_2O$ molecules to form $H_3O^+$) within the gel particle to form a soft gel. As discussed above, these soft gel particles have a tendency to agglomerate as the slurry gets denser and when the material is packed on a filter during filtration or on trays during drying.

Using at least one additive preferably forms new zirconium polymeric species in solution having a reduced number of coordinated water molecules and a high polymer unit so that when these Zr polymeric species react with phosphoric acid, the problems described above that arise from excessive hydration do not occur. In particular, the reaction of zirconium ions with phosphate is slowed, which allows for the concentration of reactants to be more easily controlled, thereby allowing for the particle size and/or particle size distribution of the particles formed by precipitation to be controlled. Because of the reduced water content, the particles formed by precipitation are harder and less prone to agglomeration and have a more refined molecular structure. If the additive that is used also has properties of an emulsifying agent, it is possible to improve the shape of the particles formed by precipitation from irregular to roughly spherical. Doing so may reduce the agglomeration problem during drying, allowing for the formation of a free-flowing powder. Even if the particle size is kept small, the flow performance for column application can be improved.

Except as otherwise provided herein, the synthesis of zirconium phosphate particles by the sol-gel process may be carried out according to known sol-gel techniques. For example, the aqueous solution used to initially dissolve the zirconium oxychloride can be water purified to remove ionic impurities such as trace metals by reverse osmosis (RO water) or by any other method that provides a low enough level of contaminants to be acceptable for the intended end use of the zirconium phosphate particle or may be deionized water. For carrying out the sol-gel precipitation, either phosphoric acid or a salt solution of phosphate can be used, except that at a high pH, the use of a phosphate salt results in a product with a reduced ammonium capacity.

The additive used in the present invention is capable of displacing water molecules that are coordinated to zirconium ions in an aqueous solution of zirconium oxychloride and that can preferably bridge zirconium ions to form a water soluble polymer species. The identity of the additive is not critical, since the additive is not incorporated into the final product. More than one type of additive can be used, e.g., mixtures. The additive should also be selected so that it can be displaced from the zirconium ions during the reaction with phosphoric acid or phosphate that forms zirconium phosphate. The additive can be a solid, liquid, and/or gas. The additive can be a compound, mixture, polymer, and the like. Compounds containing oxygen atoms are particularly useful in the present invention since oxygen can form strong bonds with zirconium. Accordingly, additives that are preferred in the present invention include inorganic and organic compounds that contain oxygen atoms that are positioned in the compound so that they are available to displace coordinated water molecules and so that zirconium atoms can be bridged to form polymeric species. The additive can also lead to the formation of polymer species that are preferably soluble in water.

Examples of additives that can be used in the present invention include inorganic substances, e.g., compounds, such as sulfates, e.g., sodium sulfate or sulfuric acid, and carbonates, and organic substances, e.g., compounds, such as alcohols, polyalcohols such as glycerol, sorbitol or mannitol, carboxylates, carboxylic acids such as acetic acid or hexanoic acid or polycarboxylic acids, ketones, aldehydes, or organic sulfates such as dodecyl sulfate, and peroxides such as hydrogen peroxide. Additives that act as dispersants or surfactants are particularly useful. For example, sodium dodecyl sulfate, which can act as a surfactant, is especially useful to enhance the crystallinity and ammonium capacity of the zirconium phosphate. It is believed that surfactants improve crystallinity of ZrP through the micelle structure formation of the zirconium polymeric complex to react with phosphate in a more orderly array. Dispersants such as glycerol, polyvinyl alcohol, tartaric acid, and the like emulsify and disperse ZrP particles to avoid agglomeration and hence control particle size of product. Specific, non-limiting examples of additives that can be used are sodium sulfate, glycerol, isopropanol, sodium carbonate, sodium lauryl sulfate (SDS), tartaric acid (typically as a DL racemic mixture), polyvinyl alcohol, 2-amino-2-methyl-propanol, hydroxypropyl cellulose, AEROSOL 22 (tetrasodium N-(1,2-dicarboxyethyl)-N-octadecyl sulfosuccinamate), TRITON 100 (octylphenoxypolyethoxy(9-10) ethanol), RHODASURF ON-870 (polyethoxylated(20) oleyl alcohol), TETRONIC 1307 (ethylenediamine alkoxylate block copolymer) and mixtures of any of these. If zirconium phosphate particles are to be used for purposes such as dialysis, a non-toxic additive, or an additive that has an acceptably low level of toxicity, should preferably be used. For example, glycerol, sodium sulfate, AEROSOL 22, DL tartaric acid, polyvinyl alcohol, sodium lauryl sulfate, hydroxypropyl cellulose and TETRONIC 1307 are considered to be non-toxic, particularly at the levels that they may be residually present in the zirconium phosphate particles. Additional specific, non-limiting examples of additives are a combination or mixture of sodium sulfate and glycerol, a combination or mixture of sodium sulfate and sodium lauryl sulfate, a combination or mixture of sodium sulfate and tartaric acid, or a combination or mixture of sodium sulfate and tetrasodium N-(1,2-dicarboxyethyl)-N-octadecyl sulfosuccinamate or combinations thereof.

Typical examples of additives and the zirconium polymer species formed in a zirconium oxychloride solution are as follows:

TABLE 1

Additives

TYPICAL ZR POLYMERIC SPECIES IN SOLUTION

INORGANIC ADDITIVES

1. Sulfates (sulfuric acid, sodium sulfate, etc.)

$$HO-Zr(H_2O)(H_2O)-O-S(O)(O)-O-Zr(H_2O)(H_2O)-O-S(O)(O)-O-Zr$$

TABLE 1-continued

Additives

TYPICAL ZR POLYMERIC SPECIES IN SOLUTION

2. Carbonate

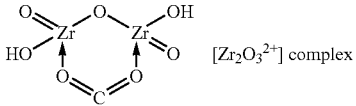  [Zr$_2$O$_3^{2+}$] complex

ORGANIC ADDITIVES

1. Alcohol ROH

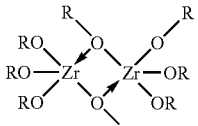

2. Glycerol

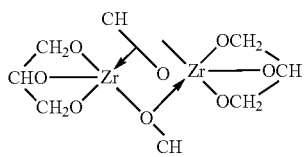

3. Carboxylate or carboxylic acid

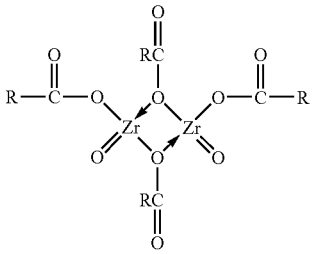

4. Ketones; aldehydes
5. Organic sulfates (sodium lauryl sulfate)

A solution wherein the additive forms a complex with zirconium ions may be formed by adding the additive to a solution containing zirconium oxychloride or by adding zirconium oxychloride to a solution containing the additive. In other words, the order of addition of the additive and the zirconium oxychloride to an aqueous solvent is not critical.

The same results of displacing coordinated water molecules and forming polymeric species can also be accomplished using fluorine-containing compounds as an additive. Examples of fluorine compounds include, but are not limited to, hydrofluoric acid and sodium fluoride, other acids containing fluorine or an alkali metal containing fluorine.

According to a method of the present invention, the quality of zirconium phosphate particles obtained by sol gel precipitation can optionally be improved by adjusting the pH of the phosphoric acid solution used. For example, the precipitating agent used in the method of the present invention can be orthophosphoric acid that is titrated with a base, like NaOH, to a pH of from about 1 to about 4. The partially titrated phosphoric acid can lower the acidity of the sol gel ZrP and thereby reduce the water of hydration. Otherwise, lattice H$^+$ can combine with H$_2$O to form hydronium ions. Thus, carrying out sol gel precipitation at a higher pH of phosphate helps to promote the hardening of the ZrP gel. However, carrying out the precipitation reaction at an alkaline pH is less preferred because zirconium phosphate precipitated by alkaline phosphate can have poor ammonia adsorption properties. This technique is preferably carried out in conjunction with the use of at least one additive, as described above.

The present invention also relates in part to a method of synthesizing zirconium phosphate particles by sol gel precipitation wherein the particle size and/or particle size distribution of the zirconium phosphate particles obtained are controlled by controlling the rate at which the solution of zirconium oxychloride (which can be an additive-containing solution as described above) is added to the reaction vessel, the rate at which the solution of phosphoric acid is added to the reaction vessel, the concentration of zirconium oxychloride and/or phosphoric acid in the reaction vessel, and/or the speed and manner of agitation of the reaction mixture. In particular, it has been found that the particle size obtained by sol gel precipitation is partly dependent upon the concentration of the reactants. When a solution of zirconium oxychloride is added to a solution of phosphoric acid, the concentration of phosphoric acid decreases as the reaction proceeds, leading to the possible formation of increasingly smaller particles. As a result, an undesirably wide range of particle sizes may be produced. To prevent this from possibly happening, both reactants, zirconium oxychloride and phosphoric acid, can be added to a reaction vessel simultaneously (or nearly simultaneously) and the addition can be stretched out over a period of time, such as, for example, ten to thirty minutes or more, thereby allowing the concentration of phosphoric acid in the reaction solution to remain steady and controllable throughout the precipitation process. As a further example, a portion of a solution of phosphoric acid can be added to a reaction vessel, and the zirconium oxychloride solution and the remainder of the phosphoric acid solution can be added to the reaction vessel simultaneously at controlled rates, again allowing the concentration of phosphoric acid in the reaction solution to remain steady and controllable throughout the precipitation process.

In addition to the simultaneous addition of zirconium oxychloride and phosphoric acid solutions, other parameters, including the manner of addition of the zirconium oxychloride solution and the manner of mixing of the reactants, can be controlled to provide a more efficient reaction and to control the particle size range. For example, a spray head can be used as the inlet for the zirconium oxychloride solution so that the zirconium oxychloride solution is added to the reaction vessel in the form of droplets, thereby providing a more efficient reaction. Further, the reaction vessel can be equipped to agitate the reactants as they are added to the reaction vessel and as the reaction proceeds, thereby providing for more efficient mixing and avoiding differences in particle sizes caused by differing concentrations of reactants in different sections of the reaction vessel. For example, the reaction vessel may include an agitator, such as, for example, an agitator having more than one set of blades attached to a shaft at different levels, so that the reactants in the reaction vessel are thoroughly mixed at all levels. As a particular example, a multi-impeller agitator may be used, such as an agitator that has three sets of blades, each set attached to a shaft at a different level. The use of an agitator to control or reduce agglomeration is optional. If an agitator is used, commercial agitators, including multi-impeller agitators, can be used. With a multi-impeller agitator, a low agitation speed, such as, for example 20-40 rpm, is preferred to avoid agglomeration without causing a break-up of gel particles. With a single-impeller agitator, a speed of about 60-70 rpm, for example, may be used. For any given agitator, the optimum speed is dependent on variables such as the tank size, shape, baffles, impeller size, and the like. Other methods of agitation or mixing may be used.

Appropriate process control methods can be used to ensure a suitable concentration range of reactants and flow rates for the precipitation process so that a desirable particle size range or distribution can be obtained. As an example, a desirable particle size distribution for zirconium phosphate particles to be used in a sorbent dialysis cartridge is as follows: less than 20% in the range of >60-120 microns (e.g., 0.1% to 19.5%, or 0.5% to 15%, or 1% to 10%), more than 80% in the range of 30-60 microns (e.g., 80.5% to 99.9%, or 85% to 99%, or 90% to 99%), and less than 10% in the range of less than 30 microns (e.g., 0.1% to 9.5%, or 0.5% to 9%, or 1% to 5%). Other particle size distributions and ranges can be used. To achieve this particle size distribution, and as an example, zirconium oxychloride solution containing sodium sulfate and glycerol and a phosphoric acid solution may be formed as follows. The zirconium oxychloride solution may contain zirconium oxychloride at its saturation point (for example, 4 kg ZOC crystals in 2.4 L water) since the size of polymeric units will increase as the concentration increases. The amount of $Na_2SO_4$ may be the maximum based on solubility in the ZOC solution (for example, about 300-500 gm, or preferably 500 gm in the ZOC solution described herein) to provide the maximum reduction in the amount of coordinated water in the Zr complex ions and suppress the degree of gelation. The amount of glycerol in the solution described herein may typically be in the range of 200-800 gm. An excess amount of glycerol can reduce the particle size too much by excessive emulsification, thereby producing many fine particles. An insufficient amount of glycerol can result in an elevated degree of agglomeration and a higher percentage of particles in the larger size range, 80-120 microns. A typical solution of phosphoric acid may contain 4.52 kg 76% $H_3PO_4$+8 L water (±1 L). The molar ratio of ZOC to phosphate or $H_3PO_4$ may be about 1:3±0.2. A specific non-limiting example of a ZOC solution formulation is 4 kg ZOC crystal powder in 2.4 liters deionized water or RO water; 500 gm $Na_2SO_4$ powder (preferably 98-99% pure); and 800 gm glycerol (preferably 98% pure). Another specific non-limiting example of an ZOC solution formulation is 4 kg ZOC crystal powder in 2.4 liters deionized water or RO water; 300 gm $Na_2SO_4$ powder, and 200 gm glycerol. As discussed in Example 8, below, this ZOC solution formulation, when combined with a high agitation speed with a single-impeller agitator for the reaction with $H_3PO_4$, was found to provide ZrP particles having the desired particle size distribution and provided optimum cartridge performance. The amounts given for the typical solution may, of course, be scaled up or down by maintaining the same proportion of reactants. Particle size control for use in sorbent dialysis cartridges may also be achieved by additional milling, if necessary, to meet cartridge performance requirements.

The flow rate for the phosphoric acid solution may be 250-290 ml/min for an addition time of 25-30 minutes, and the flow rate of the ZOC solution may be 150-180 ml/min for an addition time of 15-30 minutes. The flow rate is provided for the solution described above and may be scaled up or down if a different amount of reactants is used. A higher flow rate of the phosphoric acid increases its steady state concentration in the reaction bath and produces harder stable crystalline ZrP particles. Conversely, a lower flow rate produces a more fragile product. As a specific example, the addition time of the reactants may be 30 minutes. Other flow rates and times can be used.

The sol gel zirconium phosphate particles in a slurry formed by a method according to the present invention may be stabilized by an immediate titration to raise the pH of the slurry. For example, the slurry may be titrated with a base, such as 50% NaOH, to bring the pH up to a range of about 1-2. (Typically, the pH of the slurry when formed is close to 0.1) Then, after allowing the zirconium phosphate particles to settle and harden further, the slurry can be titrated slowly to a higher pH, such as pH 5.5 or pH 6 to obtain the finished product. The partial titration provides an immediate reduction in the acidity of the material, which may otherwise induce the adsorption of water of hydration (since lattice $H^+$ can combine with $H_2O$ to form hydronium ions) and a softening of the gel. The advantage to performing the titration slowly and in stages is that the rapid addition of alkali can cause the rapid formation of water within the gel particles, which can burst the particles and produce an excessive number of fines. For the specific use of zirconium phosphate particles in sorbent dialysis cartridges, the second titration is preferable to a pH of 5.5 to obtain the optimum $Na^+$ content in the product due to the presence of $Na^+$ and $PO_4$ ions already present in the slurry.

Because sol gel precipitation in the phosphate concentration range used in the present invention tends to be a fast reaction at room temperature, even when an additive is used, the techniques described above can be carried out without heating above the ambient temperature. Typically, a thermal treatment of the sol gel product after precipitation at room temperature is not essential. However, a thermal treatment carried out in water may be helpful to improve the molecular structure of the zirconium phosphate particles by enhancing crystallinity. Thermal treatment may improve the crystal structure of ZrP by promoting an oxolation reaction as follows:

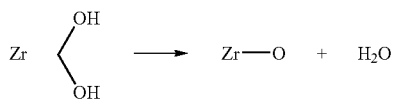

and by aiding the release of ionic impurities from the zirconium phosphate lattice formed in the sol gel precipitation. For example, if a sulfate-containing compound such as sodium sulfate is used as the additive in the formation of zirconium phosphate, a thermal treatment of the sol-gel product in water may help to release residual sulfate from the zirconium phosphate lattice. As an example of how the thermal treatment may be carried out, after zirconium phosphate has been formed by sol gel precipitation, the reaction slurry may be filtered and washed to remove chloride, excessive phosphoric acid, sulfate and additive chemicals. The filter cake obtained by filtration may then be transferred to a bath of deionized water (or RO water) and the slurry may be agitated for a short time (first wash). The filtration and washing may be repeated, for instance, until the total dissolved solids level (TDS level) in slurry is below 1200 ppm. The filter cake may be transferred to a bath of deionized water (or RO water) in a heating vessel equipped with an agitator and, with a moderate agitation speed, the slurry may be heated at moderate rate to about 180-185° F. (about 82-85° C.) with the temperature maintained in this range for 1 hour or longer. Then, the heated slurry may be allowed to cool to room temperature and the volume may be adjusted with water. Thereafter, the slurry may be titrated from a starting pH of about 1.8 to a desired pH, such as a pH of 5.75; pH 6; or pH 6.25 (or ranges therebetween) with a base, such as 50% NaOH, to obtain ZrP products of different $Na^+$ contents and acidity. The titrated ZrP may then be washed and filtered repeatedly with deionized water (or RO water) until the TDS level in the slurry is below 500 ppm. The filter cake after the final wash may then be transferred to a tray dryer and the titrated product may be dried to 14-18% loss on drying by moisture balance (LOD) at a temperature of about 160°-180° F. (71°-81° C.). The final product can be in the form of free-flowing powder, for instance, in the target particle size range of 30-60 µm and can be without agglomeration (or less than 1%).

The present invention further relates to a composition formed as an intermediate in the method of the present invention by combining a zirconium oxychloride solution with an oxygen-containing additive to form a water-soluble polymer, as described above. The amount of oxygen-containing additive depends on the particular additive and can be readily determined by performance studies. The amount of oxygen-containing additive can be a minimum amount that is effective to improve the particle size of the product.

The present invention, in at least one embodiment, relates to zirconium phosphate particles having the following characteristics: a particle size distribution of less than 20% in the range of >60-120 microns, more than 80% in the range of 30-60 microns, and less than 10% in the range of less than 30 microns, an ammonia capacity of 16-17 mg $NH_4$—N/gm ZP, and an $Na^+$ content of 3.8-6.2%. A dialysis cartridge comprising a cartridge that contains the zirconium phosphate particles is also an embodiment of the present invention.

The dialysis cartridge can be a cartridge that contains the zirconium phosphate particles, wherein the zirconium phosphate particles are present as at least one layer and the dialysis cartridge further can comprise at least one other layer(s) of sorbent material.

The ZrP of the present invention can be used in any application where ZrP is used and can be used as the ZrP layer or as an additional ZrP layer in sorbent cartridges described in U.S. Published Patent Application No. 2002-0112609 and U.S. Pat. No. 6,878,283 B2, and in Sorb's REDY cartridge (e.g., see "Sorbent Dialysis Primer," COBE Renal Care, Inc. Sep. 4, 1993 edition, and "Rx Guide to Custom Dialysis," COBE Renal Care, Inc. Revision E, September, 1993), all incorporated in their entirety by reference herein. All embodiments using ZrP in these published applications are embodiments of the present application wherein the ZrP of the present invention is used. For example purposes only, various filter media sections within a tubular housing or cartridge can be used with the ZrP particles of the present invention. The housing or cartridge can include a sorbent material like a granular activated carbon section, an immobilized enzyme section, a powdered alumina ($Al_2O_3$) section, a zirconium phosphate, and/or a section that includes a mixture of hydrous zirconium oxide of the acetate form and sodium zirconium carbonate, or sodium zirconium carbonate alone. The dialysis cartridge can be a cartridge that contains as one or more layers or zones the zirconium phosphate particles, wherein the dialysis cartridge has a plurality of filter media sections (or layers) including an arrangement, starting from a first end and ending at a second end, an activated carbon section, an immobilized enzyme section, a powdered alumina section, a zirconium phosphate section, and a sodium zirconium carbonate or a mixture of hydrous zirconium oxide of the acetate form and sodium zirconium carbonate section. For hemodialysis, a filter medium adapted to remove chlorine from tap water is preferred unless highly purified water is used as a base for the dialysate. The medium can be activated carbon. Activated carbon can be used as a filter medium to bind heavy metals, oxidants, and chloramines. An immobilized enzyme such as urease can be used in a filter medium to convert urea to ammonium carbonate by enzymatic conversion. Urease can be immobilized by adsorption, covalent bonding, intermolecular cross-linking, entrapment within cross-linked polymers, microencapsulation, and containment within a semipermeable membrane device. Alumina ($Al_2O_3$), activated carbon, anion exchange resins, and diatomaceous earth can be used as adsorbents. Urease can be used to covalently bond water-insoluble polymers to form enzyme-polymer conjugates via activation procedures or reactive polymers. Multifunctional reagents, for example, glutaraldehyde and hexamethylene diamine can be used to affect intermolecular cross-linking of urease. Urease can be entrapped within a cross-linked polymer, such as, for example, polyacrylamide gel. Urease can be microencapsulated using, for example, nylon, cellulose nitrate, ethyl cellulose, or polyamide. Urease can be contained within some permeable membrane device, such as, for example, AMICOM ultra-filtration cells, available from Fisher Scientific, Pittsburgh, Pa., or DOW hollow fiber beaker device, from The Dow Chemical Co., Midland, Mich. The use of activated carbon to remove chlorine, if used, can precede the immobilized enzyme medium because chlorine can deactivate the enzyme. Cation exchange materials can be used to bind ammonium, calcium, magnesium, potassium, and other cations as well as toxic trace metals in tap water. Another function of these filter media can be to convert carbonate from urea hydrolysis to bicarbonate. Such cation exchange materials can include zirconium phosphate, titanium phosphate, or zeolite. Anion exchange filter media bind phosphate, fluoride, and other heavy metals. By-products of the anion exchange filter media can include acetate and bicarbonate, which also corrects for metabolic acidosis of a patient's blood. Such filter media can include hydrous zirconium oxide of the acetate form, hydrous silica, stannic oxide, titanium oxide, antimonic acid, hydrous tungsten oxide, or sodium zirconium carbonate.

The following examples are given to illustrate the nature of the invention. It should be understood, however, that the present invention is not to be limited to the specific conditions or details set forth in these examples.

EXAMPLES

Example 1

Sodium Sulfate as Additive

A solution of diluted phosphoric acid was made up by mixing 160 gm of 85% orthophosphoric acid with 700 ml deionized water in vessel A. A solution of zirconium oxychloride (ZOC)/sulfate was made up by first dissolving 200 gm of ZOC, in the form of powder crystals, in 120 ml deionized water in vessel B to form a ZOC solution, adding 25 gm of $Na_2SO_4$ to the ZOC solution and then agitating to form a clear solution of a zirconium-sulfate complex. Next, 100 ml of the diluted phosphoric acid was transferred from vessel A to a reactor vessel C fitted with an agitator with 3 sets of blades at different levels. With a moderate agitator rate in reactor vessel C, and at room temperature, the rest of the phosphoric acid (from vessel A) and the zirconium-sulfate complex solution (from vessel B) were pumped into reactor vessel C at flow rates of about 23 ml/min and 8.3 ml/min, respectively, via capillary tubings so that the addition and mixing of both components could be completed at about the same time (in approximately 30 minutes). In the reaction vessel, the soluble zirconium-sulfate complex was allowed to react with the phosphoric acid, which displaced the sulfate from the zirconium-sulfate complex to form a ZrP sol gel precipitate of uniform particle size in the range 100-150 microns. (In additional experiments, it was found that the particle size range could be lowered to the appropriate range for column application (30-60 microns) by reducing the concentration of phosphoric acid or the flow rate of the reactants and by increasing the agitation rate.) After the addition was complete and while maintaining the agitation at the same speed, the slurry of the precipitate was titrated to a pH of about 1-2 by adding about 40 ml of 50% NaOH. Then, the agitation was stopped to allow the gel precipitate to settle and harden further. Then, the slurry was titrated to a pH of 6 with further agitation. After titration was complete, the material was allowed to sit again for 30 minutes without agitation, and then the pH of the slurry was rechecked. When the pH was found to be stable in the range of 5.75-6.0, further agitation was discontinued and the slurry was filtered by a Buchner funnel using Whatman #1 filter paper. The filter cake was then washed with a sufficient amount of deionized water to remove the chloride, sulfate, excessive phosphate and $Na^+$ until the TDS (total dissolved solids) in the filtrate was below 500 ppms. Then, the filter cake was transferred to a tray dryer and the product was dried at 120° F.-160° F. until the moisture level of 16-20% LOD (Loss on Drying by moisture balance) was obtained. The product was a free-flowing powder of desirable particle size range (100-150 microns in this test) free of agglomeration upon drying.

Example 2

Glycerol as Additive

The steps described in Example 1 were repeated, except that a solution of a zirconium-glycerol complex formed by adding 20 gm glycerol to the ZOC solution was used instead of a solution of a zirconium-sulfate complex. Smooth, oval shaped particles of a particle size in the range 20-40 microns were obtained during the precipitation process. Despite the smaller particle size, there were no problems of flow resistance during filtration and column application of the finished product because of the smooth shape of the particles formed by the emulsification effect of glycerol. Furthermore, upon drying, the hard gel ZrP formed a free-flowing powder without agglomeration. The product samples were tested to have the following properties: a particle size distribution of less than 30% in the range of >60-120 microns, 70% or higher in the range of 30-60 microns, and less than 10% in the range of less than 30 microns, an ammonia capacity of 16-17 mg $NH_4$—N/gm ZP, and an $Na^+$ weight content of 5.2-6.2 wt %.

Example 3

Sodium Carbonate as Additive

The steps described in Example 1 were repeated, except that a solution of a zirconium-carbonate complex formed by adding 25 gm of sodium carbonate to the ZOC solution was used instead of a solution of a zirconium-sulfate complex. The use of sodium carbonate had the same effect on process performance and particle size of product as the use of sodium sulfate in Example 1.

Example 4

No Additive; Titration of Phosphoric Acid

The steps described in Example 1 were repeated, except that the precipitating agent was phosphoric acid titrated to pH 4 with NaOH, and except that a ZOC solution was used alone without an additive. A reduction of agglomeration was observed, in comparison to the product obtained by using unadjusted phosphoric acid and a solution of ZOC alone, but agglomeration was not completely eliminated.

Example 5

Isopropanol as Additive

The steps in Example 1 were repeated, except that a solution of a zirconium-isopropanol complex formed by adding 40 gm of isopropanol to the ZOC solution was used instead of a solution containing a zirconium-sulfate complex. A reduction of agglomeration during the process was observed, as in Example 1, and the product was a free-flowing powder having a particle size range of 100-150 microns.

Example 6

Sodium Sulfate and Glycerol as Co-additives

The steps in Example 1 were repeated, except that a zirconium complex solution formed by using both $Na_2SO_4$ and glycerol as additives was used instead of a solution containing only a zirconium-sulfate complex.

A solution was made up by first dissolving 200 gm of powder crystals of ZOC in 120 ml deionized water to form a ZOC solution and then adding 25 gm NaSO$_4$ to the solution. After agitating to form a clear solution of zirconium-sulfate complex ion, 25 gm glycerol was added and mixed well with the solution. (As discussed in Example 2, glycerol can serve as an emulsification agent to smooth the shape of the particles as well as serving to form a complex with zirconium ions.) The phosphoric acid used in this example was titrated to pH 2 with 50% NaOH to further reduce agglomeration during the reaction. In particular, a diluted phosphoric acid solution was made up by first mixing 173.3 gm Technical Grade phosphoric acid (76%) with 400 ml deionized water in a vessel and then slowly titrating the acid with 56 ml 50% NaOH until the pH was about 2.0. Then, 100 ml of the diluted acid was transferred from the vessel to a 1500 ml reactor vessel fitted with an agitator with 3 sets of blades at different levels. With a high agitator rate and at room temperature, the rest of phosphoric acid and the zirconium sulfate/glycerol complex solution were pumped in at flow rates of about 20 ml/min and 8 ml/min respectively so that the addition and mixing of both components could be completed at about the same time (in approximately 30 minutes). The hard gel ZrP precipitate that formed had a particle size with a uniform range of 30-60 microns, a size that is suitable for column applications. The smaller size (in comparison to the particle size obtained in Example 1) is believed to be due to the high agitation speed and emulsification effect of glycerol. After the precipitation was complete, the slurry was titrated to a pH of 6.0, followed by washing and drying of the product as in Example 1. The ZrP produced was a free-flowing powder of particle size range 30-60 microns free of agglomeration upon drying and having ammonia adsorption capacity of about 17 mg NH$_4$—N/gm ZrP.

Example 7

Sodium Carbonate and Glycerol as Additives

The steps in Example 6 were repeated, except that 25 gm of sodium carbonate was used instead of Na$_2$SO$_4$ as an additive to the ZOC solution. The same process performance and ZrP product quality were obtained as in Example 6.

Example 8

Scale-up with Sodium Sulfate and Glycerol as Additives and with Variations of Process Parameters Studies were carried out to evaluate the process performance of the scale-up synthesis of ZrP from ZOC by sol gel precipitation and to evaluate the ZrP quality based on cartridge performance tests. For the scale-up, the following materials were used: zirconium oxychloride (ZOC) from Southern Ionics, Inc., technical grade phosphoric acid 76%, sodium sulfate as additive, glycerol as additive, RO Water or deionized water, and 50% NaOH for titration of ZrP. The following process equipment was used: a 12 liter vessel for dilute phosphoric acid preparation (vessel A), a 6 liter vessel for ZOC/sulfate complex solution preparation (vessel B), a reactor vessel fitted with multi-impeller blades agitator (vessel C), an agitator motor, delivery lines for delivering phosphoric acid and ZOC solution including peristaltic pumps (Watson Marlow 100-400 ml/min) and a spray nozzle for ZOC at the inlet of reactor, a vacuum filtration unit (vacuum, pump, filtration flask, Buchnel funnel and Whatman #541 filter paper), a pH meter, a TDS meter and a tray dryer.

As a baseline, a ZrP was synthesized on a pilot scale by the following procedure: A solution of diluted phosphoric acid was made up by mixing 4.52 km of 76% H$_3$PO$_4$ with 8 L deionized or RO water in vessel A. A solution of zirconium oxychloride (ZOC)/sulfate complex was made up by first dissolving 4 kg ZOC, in the form of powder crystals, in 3 L deionized or RO water in vessel B to form a ZOC solution, and then adding 500 gm Na$_2$SO$_4$ to the ZOC solution and then agitating to form a clear solution of a zirconium-sulfate complex. Next, 800 gm glycerol was added and mixed to form a clear solution. Next, 1 L of the dilute phosphoric acid was transferred from vessel A to a reactor vessel C fitted with an agitator with 3 sets of impeller blades attached to the shaft at different levels. With a moderate agitator rate in reactor vessel C, and at room temperature, the rest of the phosphoric acid (from vessel A) and the zirconium-sulfate complex solution (from vessel B) was pumped into reactor vessel C at flow rates of about 460 ml/min and 167 ml/min, respectively, so that the addition and mixing of both components was completed at about the same time (in approximately 30 minutes). A spray nozzle was used at the inlet to the reactor of the ZOC delivery line so that ZOC solution was in the form of droplets before it reacted with the phosphoric acid. The soluble zirconium-sulfate complex reacted with the phosphoric acid, so that the sulfate was displaced from the zirconium-sulfate complex, and a ZrP sol gel precipitate of uniform particle size was formed in the reaction vessel. After the addition was complete and while maintaining the agitation at the same speed, the ZrP slurry formed thereby was diluted with 4 L deionized or RO water to dilute the slurry, and the slurry was titrated to a pH of about 5.75-6.00 by adding about 2.9 L of 50% NaOH gradually, monitored by a pH meter. Then, when the final pH was stable, agitation was stopped and the gel precipitate was allowed to settle and harden for one hour. Then, with restarted agitation, the slurry was filtered by a Buchner funnel using Whatman #541 filter paper. The filter cake was then washed with a sufficient amount of deionized or RO water to remove the chloride, sulfate, excessive phosphate and Na$^+$ until the TDS (total dissolved solids) in the filtrate was below 500 ppms. Then, the filter cake was transferred to a tray dryer and the product was dried at 120° F.-160° F. until the moisture level of 16-20% LOD (Loss on Drying by moisture balance) was obtained. The product should form a free-flowing powder of desirable particle size range free of hard agglomerations upon drying.

In order to study the effects of minor adjustments in formulation and process conditions, 10 batches of sol gel ZrP (approximately 4 kg./batch) were made with minor adjustments in formulation and process condition (amount of additives and ZOC concentration, phosphoric acid concentration and molar mixing ratio, feed rate of reactants, agitation speed, dilution of ZrP slurry before titration, and the like). In all of the batches, the following process conditions were not changed: Completion time of mixing: 30 minutes; Dilution of ZrP slurry before titration: 4 L H$_2$O; and amount of NaOH required for titration and pH: ~3 L, pH 5.5. Each batch was then evaluated based on agglomeration during precipitation, the amount of fine particles and difficulty of filtration and product quality based on particle size range (30-60 microns being ideal), ammonia adsorption capacity, and cartridge performance. The particular batches are shown in Table 1:

TABLE 1

Setting up Process Formulation and Condition for the Serial Tests

| Test No. | Formulation & Concentration of Reactants | Feed Rate of Reactants | Agitation Speed | TDS | LOD |
|---|---|---|---|---|---|
| 1 | $H_3PO_4$<br>4.52 kg 76% $H_3PO_4$ + 8 L $H_2O$<br>(2 L initial) | 290 ml/min | moderate-high<br>50 RPM<br>(3 impeller) | 700 ppm | 17% |
|   | ZOC<br>4 kg ZOC + 2.4 L $H_2O$<br>500 gm $Na_2SO_4$<br>800 gm glycerol | 180 ml/min | | | |
| 2 | $H_3PO_4$<br>4.52 kg 76% $H_3PO_4$ + 8 L $H_2O$<br>(2 L initial) | 290 ml/min | moderate<br>40 RPM<br>(3 impeller) | 600 ppm | 18% |
|   | ZOC<br>4 kg ZOC + 2.4 L $H_2O$<br>500 gm $Na_2SO_4$<br>700 gm glycerol | 180 ml/min | | | |
| 3 | $H_3PO_4$<br>4.52 kg 76% $H_3PO_4$ + 8 L $H_2O$<br>(2 L initial) | 290 ml/min | moderate<br>40 RPM<br>(single impeller) | 600 ppm | 18% |
|   | ZOC<br>4 kg ZOC + 2.4 L $H_2O$<br>500 gm $Na_2SO_4$<br>800 gm glycerol | 180 ml/min | | | |
| 4 | $H_3PO_4$<br>4.52 kg 76% $H_3PO_4$ + 8 L $H_2O$<br>(2 L initial) | 290 ml/min | moderate<br>40 RPM<br>(single impeller) | 700 ppm | 19% |
|   | ZOC<br>4 kg ZOC + 2.4 L $H_2O$<br>500 gm $Na_2SO_4$<br>700 gm glycerol | 180 ml/min | | | |
| 5 | $H_3PO_4$<br>4.52 kg 76% $H_3PO_4$ + 7 L $H_2O$<br>(3 L initial) | 220 ml/min | moderate<br>40 RPM<br>(single impeller) | 450 ppm | 16% |
|   | ZOC<br>4 kg ZOC + 2.4 L $H_2O$<br>470 gm $Na_2SO_4$<br>600 gm glycerol | 180 ml/min | | | |
| 6 | $H_3PO_4$<br>4.52 kg 76% $H_3PO_4$ + 7 L $H_2O$<br>(3 L initial) | 220 ml/min | moderate<br>40 RPM<br>(single impeller) | 700 ppm | 19% |
|   | ZOC<br>4 kg ZOC + 2.4 L $H_2O$<br>400 gm $Na_2SO_4$<br>500 gm glycerol | 180 ml/min | | | |
| 7 | $H_3PO_4$<br>4.52 kg 76% $H_3PO_4$ + 7 L $H_2O$<br>(3 L initial) | 220 ml/min | moderate-high<br>50 RPM<br>(single impeller) | 500 ppm | 17% |
|   | ZOC<br>4 kg ZOC + 2.4 L $H_2O$<br>400 gm $Na_2SO_4$<br>400 gm glycerol | 180 ml/min | | | |
| 8 | $H_3PO_4$<br>4.52 kg 76% $H_3PO_4$ + 7 L $H_2O$<br>(3 L initial) | 220 ml/min | moderate-high<br>50 RPM<br>(single impeller) | 580 ppm | 20% |
|   | ZOC<br>4 kg ZOC + 2.4 L $H_2O$<br>400 gm $Na_2SO_4$<br>300 gm glycerol | 180 ml/min | | | |
| 9 | $H_3PO_4$<br>4.52 kg 76% $H_3PO_4$ + 7 L $H_2O$<br>(3 L initial) | 220 ml/min | high<br>70 RPM<br>(single impeller) | 650 ppm | 18% |
|   | ZOC<br>4 kg ZOC + 2.4 L $H_2O$<br>300 gm $Na_2SO_4$<br>200 gm glycerol | 180 ml/min | | | |
| 10 | $H_3PO_4$<br>4.52 kg 76% $H_3PO_4$ + | 220 ml/min | higher<br>80 RPM | 600 ppm | 18% |

TABLE 1-continued

Setting up Process Formulation and Condition for the Serial Tests

| Test No. | Formulation & Concentration of Reactants | Feed Rate of Reactants | Agitation Speed | TDS | LOD |
|---|---|---|---|---|---|
| | 7 L H$_2$O (3 L initial) ZOC 4 kg ZOC + 2.4 L H$_2$O 300 gm Na$_2$SO$_4$ 200 gm glycerol | 180 ml/min | (single impeller) continued agitation for 1 hour after reaction | | |

In all of the test batches, there was no agglomeration during precipitation, no agglomeration upon drying and no filtration difficulty. The test batches were tested for product quality and cartridge performance. The fragility of particles, NH$_4$ adsorption, particle size range, and cartridge performance parameters including UNC (urea nitrogen capacity), percentage of unused ZrP and cartridge pressure. The cartridge performance parameters were tested with a REDY® D-31 sorbent dialysis cartridge in triplicate tests using a QC single pass system. The process performance and product quality data are shown in Table 2 (the test compounds are the same as those in Table 1). The process parameters are summarized in Table 2 for convenience.

TABLE 2

Evaluation of Process Performance

Process Performance Evaluation and Product Quality Evaluation

| No. | Summary of Process Parameters | Fragility of Particles | NH$_4$ Adsorption | Particle Size Range | Cartridge Performance |
|---|---|---|---|---|---|
| 1 | Additive amount in excess; agitation 50 RPM; acid dilution 8 L; initial 2 L | Fragile | 16.5 mg NH$_3$—N per gm ZrP | <10 μm >30% 30-60 μm ~50% >60 μm >10% | Test aborted because of cartridge cover damage by high pressure >50 psi |
| 2 | Additive amount in excess; agitation 40 RPM; acid dilution 8 L; initial 2 L | Fragile | 16.0 mg NH$_3$—N per gm ZrP | <10 μm >30% 30-60 μm ~50% >60 μm >10% | Gm ZrP 900 UNC 16.5 gm 20% unused ZrP pressure 21 psi |
| 3 | Additive amount in excess; agitation single impeller 40 RPM; acid dilution 8 L; initial 2 L | Fragile | 16.8 mg NH$_3$—N per gm ZrP | <10 μm >20% 30-60 μm ~60% >60 μm >10% | Gm ZrP 925 UNC 26.3 gm 1% unused ZrP but high pressure >30 psi |
| 4 | Gradual reduction of glycerol; agitation single impeller 40 RPM; acid dilution 8 L; initial 2 L | Fragile | 16.6 mg NH$_3$—N per gm ZrP | <10 μm >20% 30-60 μm ~50% >60 μm >20% | Gm ZrP 1000 UNC 22 gm 10% unused ZrP but high pressure >30 psi |
| 5 | Gradual reduction of Na$_2$SO$_4$ and glycerol; agitation single impeller 40 RPM; acid dilution 7 L; initial 3 L | Hard | 16.5 mg NH$_3$—N per gm ZrP | <10 μm >10% 30-60 μm ~60% >60 μm >20% | Gm ZrP 900 UNC 19.6 gm (low) 20% unused ZrP pressure 16 psi |
| 6 | More reduction of Na$_2$SO$_4$ and glycerol; agitation single impeller 40 RPM; acid dilution 7 L; initial 3 L | Hard | 16.5 mg NH$_3$—N per gm ZrP | <10 μm <10% 30-60 μm ~60% >60 μm >20% | Gm ZrP 900 UNC 19.3 gm (low) 20% unused ZrP pressure 11.5 psi |
| 7 | More reduction of Na$_2$SO$_4$ and glycerol; higher agitation 50 RPM; | Hard | 16.8 mg NH$_3$—N per gm ZrP | <10 μm >20% 30-60 μm ~60% >60 μm >10% | Gm ZrP 1000 UNC 25.6 gm 20% unused ZrP pressure 19.5 psi |
| 8 | Optimal use of Na$_2$SO$_4$ and glycerol; higher agitation 50 RPM; | Hard | 16.8 mg NH$_3$—N per gm ZrP | <10 μm >10% 30-60 μm ~80% >60 μm <10% | Gm ZrP 900 UNC 24.8 gm 2% unused ZrP pressure 16 psi |
| 9 | Optimal use of Na$_2$SO$_4$ and glycerol; further increase of agitation 70 RPM | Hard | 16.8 mg NH$_3$—N per gm ZrP | <10 μm >10% 30-60 μm ~80% >60 μm <10% | Gm ZrP 900 UNC 25.8 gm 2% unused ZrP pressure 19 psi |

TABLE 2-continued

Evaluation of Process Performance

| | | Process Performance Evaluation and Product Quality Evaluation | | | |
|---|---|---|---|---|---|
| No. | Summary of Process Parameters | Fragility of Particles | $NH_4$ Adsorption | Particle Size Range | Cartridge Performance |
| 10 | Optimal use of $Na_2SO_4$ and glycerol; further increase of agitation 80 RPM and time 1 hr | Hard | 16.7 mg $NH_3$—N per gm ZrP | <10 µm 30-60 µm >60 µm | >20% Gm ZrP 900 ~60% UNC 24.7 gm >10% 2% unused ZrP pressure 28 psi |

As shown in Table 2, the particle size and particle size distribution of ZrP can be controlled by using an optimal amount of additive coupled with a high agitation speed, thereby achieving a uniform particle size within the target ZrP particle size range of 30-60 microns, which is typically the optimum range for good cartridge adsorption performance. An excessive amount of additive increases the amount of fine particles (<10 microns), causing high flow resistance and back pressure of the cartridge, while an insufficient amount increases agglomeration and causes the formation of bigger particles (>6 microns) causing ammonia leakage and lower adsorption capacity (or low UNC) of the cartridge. Agitation speed and time, as well as the concentration of reactants, are also important factors to control the particle size range. A slow agitation speed increases the range of non-uniform particle size by producing more particles that are larger or smaller than the target range, whereas a high agitation speed coupled with an optimal additive amount increases the uniformity of the particles. The effects of using various amounts of additives and agitation rate on particle size distribution of product as reflected by the cartridge performance of the product are summarized by the results of Table 2, above. The cartridge test results (Tests 8, 9) indicate that particle size is controllable to meet the cartridge performance requirement as described above, and, as a non-limiting example, the optimal amount of additives for making ZrP particles on a pilot scale to be used in at least one particular sorbent dialysis cartridge has been found to be as follows: 4 kg ZOC solid/2.4 L $H_2O$; 300 gm $Na_2SO_4$ and 200 gm glycerol.

Example 9

Evaluation of Various Additives

The following general synthesis procedure was used to screen and evaluate various additives. A diluted phosphoric acid and a ZOC solution is prepared in vessel A and vessel B, respectively. The solution of diluted phosphoric acid is made up by mixing 39% by weight of 76% tech grade $H_3PO_4$ with 61% by weight of deionized water or RO water in vessel A. The ZOC is made up by mixing 57% by weight of ZOC solid powder and 34% by weight of deionized water or RO water, with the remainder being an additive, such as, for example, about 4.5% by weight sodium sulfate and about 2.4% of a surfactant/dispersant. (Specific amounts are provided in the specific examples, below). Next, about 40% of the diluted phosphoric acid is transferred from vessel A to a reactor vessel C fitted with an agitator. With a moderately high agitator rate in reactor vessel C, and at room temperature, and the ZOC solution from vessel B is pumped into reactor vessel C to mix with the phosphoric acid. Precipitation of ZrP occurs instantaneously, and the particle size is controlled by the amount of surfactant/dispersant and the agitation rate. The reacted phosphoric acid is replenished by simultaneously adding diluted phosphoric acid from vessel A. The flow rates of the diluted phosphoric acid and the ZOC solution are adjusted so that the addition of both reactants is completed at about the same time (for example, in approximately 30 minutes). The completion of the addition of phosphoric acid may be slightly ahead of the completion of the addition of the ZOC solution.

After the addition is complete, the product slurry is filtered to remove most of the chloride, excessive phosphoric acid, and additives, including sulfate. The filter cake is transferred to a bath of deionized water (or RO water) and the slurry is agitated for a short time (first wash). The filtration and washing are repeated until the TDS level in slurry is below 1200 ppm.

If a thermal treatment is carried out, this is done by filtering the ZrP after the initial wash and transferring the filter cake to a bath of deionized water (or RO water) in a heating vessel equipped with an agitator with a moderate agitation speed The slurry is heated at a moderate rate to about 180-185° F. and the temperature is maintained in this range for about 1 hour. If a reduced particle size is desired, this may be achieved by a longer treatment time at higher agitation speed. The slurry is then cooled to room temperature and the volume is adjusted with water, if necessary.

Next, the slurry is titrated with 50% NaOH from pH ~1.8 to pH 5.75; pH 6; or pH 6.25 to obtain ZrP products of different $Na^+$ contents and acidity. The titrated ZrP is then filtered and washed repeatedly with deionized water (or RO water) until the TDS level in slurry is below 500 ppm.

The filter cake is transferred after the final wash to a tray dryer and dried to 14-18% LOD at the temperature of about 160°-180° F. The final product is typically in the form of a free-flowing powder in the target particle size range of 30-60 µm without agglomeration (or less than 1%).

Use of the General Synthesis Procedure with Specific Additives

The above sol gel precipitation technique outlined above, except skipping the thermal treatment, was applied to the following specific additives. In each test, 80 gm of ZOC was used and a molar ratio of $H_3PO_4$:$ZrOCl_2$ of 3:1 was maintained. The amounts of the remaining ingredients were as specified below.

(1) Glycerol (4 gm; 6 gm per 80 gm ZOC)
(2) AEROSOL 22 or CYBREAK 4003 (0.8 gm; 1.5 gm; 2 gm; 6 gm per 80 gm ZOC)
(3) DL tartaric acid (0.5 gm; 1 gm; 1.5 gm per 80 gm ZOC)
(4) Sodium lauryl sulfate (SDS) (0.5 gm; 1 gm per 80 gm ZOC)
(5) Polyvinyl alcohol (0.5 gm; 1 gm per 80 gm ZOC)
(6) 2 amino-2 methyl propanol 95% (4 gm per 80 gm ZOC)
(7) Hydroxypropyl cellulose (0.5 gm per 80 gm ZOC)
(8) TRITON 100 (3 gm per 80 gm ZOC)
(9) RHODASURF ON-870 (4 gm per 80 gm ZOC)

(10) TETRONIC 1307 (6 gm per 80 gm ZOC)
(11) Tartaric acid/sodium sulfate (6/6 gm per 80 gm ZOC)
(12) SDS/sodium sulfate (3/6 gm per 80 gm ZOC)

The above sol gel precipitation technique outlined above, including the thermal treatment, was applied to the following specific additives:

(13) glycerol/sodium sulfate (6/6 gm per 80 gm ZOC)
(14) sodium lauryl sulfate/sodium sulfate (3/6 gm per 80 gm ZOC)
(15) Aerosol 22/sodium sulfate (4/6 gm per 80 gm ZOC)

Specific Example Using Specific Amounts

In a synthesis according to the general synthesis procedure outlined above, without thermal treatment and using tartaric acid as the additive, the ZOC solution contained 80 gm ZOC, 1.5 gm DL tartaric acid and 45 ml deionized or RO water. The diluted phosphoric acid solution contained 90.4 gm Tech Grade 76% $H_3PO_4$ and 140 ml deionized or RO water. 80 ml of the diluted phosphoric acid solution was initially added to the reactor vessel C. The ZOC solution was added to the reactor vessel C at the rate of 1.4 ml/min and the diluted phosphoric acid solution was added at the rate of 4 ml/min. The final product was in the form of a free-flowing powder with an average particle size of 60 microns and containing less than 1% agglomeration (>100 microns). The product had an ammonia adsorption capacity of 16.46 mg/gm and a packing density of 0.94 gm per cc. The yield was 101 gm.

Using the same synthesis procedure, except including 6 gm sodium sulfate in combination with the DL tartaric acid, the final product was free of agglomeration and fine particles and had a uniform particle size range of 30-60 microns. The grains were harder, reflecting an improvement in the crystallinity.

Summary of Overall Results

Zirconium phosphate particles produced with each of these additives, and with each of the specified amount of additive, were evaluated according to ammonia adsorption capacity, packing density and hardness of particles, controllability of particle size range, release or lack or release of toxic chemicals during application based on biocompatibility testing and FDA safety limit for dialysis application, and feasibility for manufacture based on acceptable process performance, economic factors (cost and yield) and process hazards and waste control. The results are shown in Table 3.

TABLE 3

Screen test of dispersants for sol gel ZrP precipitation process Basis: 80 g ZOC; ZOC concentration 80 g/48 ml $H_2O$; DIL $H_3PO_4$ concentration 90.4 g 76% $H_3PO_4$/140 ml $H_2O$

| Dispersants/ Data | Ave Particle Size | Amt. of Agglom/ Gelation | $NH_4$—N Adsorption Capacity | Packing Density gm/cc | Toxicity | Filtration Difficulty | Yield | Remarks |
|---|---|---|---|---|---|---|---|---|
| Glycerol | | | | | | | | |
| T1  4:80 | 60 μm | 0 | 17.2 mg/g | 1.048 | non-toxic at low level | none | 101 g | |
| T2  6:80 | 40 μm | 0 | 16.82 mg/g | 0.98 | | | 96 g | |
| T3  6:80 | 40 μm | 0 | 16.45 mg/g | 0.95 | | | 95 g | |
| Aerosol 22 or Cybreak 4003 | | | | | | | | |
| T1  2:80 | 40 μm | 0 | 17.06 mg/g | 0.92 | non-toxic at low level | none, but require excessive wash to remove foam | 79 g | |
| T2  1.5:80 | 50 μm | 0 | 17.1 mg/g | 0.88 | | | 115 g | |
| T3  0.8:80 | 80 μm | slight | 17.04 mg/g | 0.92 | | | 82 g | |
| T4  6:80 | 30 μm | 0 | 17.16 mg/g | 0.88 | | | 89 g | |
| T5  6:80 | 40 μm | 0 | 17.02 mg/g | 0.95 | | | 88 g | |
| DL Tataric acid | | | | | | | | |
| T1  0.5:80 | 80 μm | slight | 16.5 mg/g | 0.91 | non-toxic at low level | none | 100 g | |
| T2  1:80 | 60 μm | 0 | 16.54 mg/g | 0.95 | | | 100 g | |
| T3  1.5:80 | 60 μm | 0 | 16.46 mg/g | 0.94 | | | 101 g | |
| Polyvinyl Alcohol | | | | | | | | |
| T1  1:80 | 30 μm | 0 | 16.42 mg/g | 0.87 | non-toxic | none, but require excessive wash to remove residual PVA | 98 g | high price |
| T2  0.5:80 | 60 μm | slight | 16.5 mg/g | 0.86 | | | 94 g | |
| Sodium Lauryl Sulfate (SDS | | | | | | | | |
| T1  1:80 | 70 μm | 0 | 17 mg/g | 0.97 | non-toxic at low level | none, but require excessive wash to remove foam | 103 g | |
| T2  0.5:80 | 180 μm | slight | 16.92 mg/g | 0.97 | | | 84 g | |
| 2 Amino 2 Methyl Propanol 95% | | | | | | | | |
| T1  4:80 | 60 μm | 0 | 16.4 mg/g | 0.87 | harmful | none | 100 g | toxic for dialysis |

TABLE 3-continued

Screen test of dispersants for sol gel ZrP precipitation process Basis: 80 g ZOC; ZOC concentration 80 g/48 ml $H_2O$; DIL $H_3PO_4$ concentration 90.4 g 76% $H_3PO_4$/140 ml $H_2O$

| Dispersants/ Data | Ave Particle Size | Amt. of Agglom/ Gelation | $NH_4$—N Adsorption Capacity | Packing Density gm/cc | Toxicity | Filtration Difficulty | Yield | Remarks |
|---|---|---|---|---|---|---|---|---|
| Hydroxypropyl Cellulose | | | | | | | | |
| T1 0.5:80 | 50 μm | 0 | 16.48 mg/g | 0.90 | non-toxic | none | 85 g | high price |
| Triton 100 | | | | | | | | |
| T1 3:80 | 60 μm | 0 | 17.02 mg/g | 0.8 | harmful | none, but require excessive wash to remove foam | 82 g | toxic for dialysis |
| Rhodasurf ON-879 | | | | | | | | |
| T1 4:80 | 70 μm | 0 | 17.1 mg/g | 0.85 | harmful | none, but require excessive wash to remove foam | 84 g | toxic for dialysis |
| Tetronic 1307 | | | | | | | | |
| T1 6:80 | 50 μm | 0 | 17.16 mg/g | 0.82 | non-toxic | none, but require excessive wash to remove foam | 89 g | low packing density |
| Glycerol/ Sodium Sulfate | | | | | | | | |
| T1 6:6:80 | 50 μm | 0 | 16.6 mg/g | 0.98 | non-toxic | none | 87 g | |
| Tartaric Acid/Sodium Sulfate | | | | | | | | |
| T1 6:6:80 | 40 μm | 0 | 16.5 mg/g | 0.8 | non-toxic at low level | none | 82 g | low packing density |
| Sodium Lauryl Sulfate/Sodium Sulfate | | | | | | | | |
| T1 3:6:80 | 40 μm | 0 | 16.6 mg/g | 0.8 | non-toxic at low level | none | 76 g | low packing density |
| Control: ZrP made from ZBS | 50 μm | — | 16.8 mg/g | 1.32 | — | — | — | |
| Glycerol/Sodium Sulfate 6:6:80 with Thermal Treatment | 50 μm | 0 | 17.1 mg/g | 1.05 | non-toxic | none | 87 g | |
| Sodium Lauryl Sulfate/Sodium Sulfate 3:6:80 with Thermal Treatment | 30 μm | 0 | 16.9 mg/g | 0.84 | non-toxic at low level | none | 88 g | low packing density |

To summarize, all of the surfactants and dispersants tested in this study can prevent agglomeration of ZrP during the reaction with phosphoric acid and control the particle size of the product. All these surfactants contain functional groups with oxygen atoms in them, which tend to form soluble zirconium polymeric species with ZOC and remove coordinated water molecules from Zr that may cause gelation of ZrP. Generally, dispersants with higher emulsification strength were more effective in controlling particle size to the appropriate range of 30-60 microns when assisted by optimum adjustment of the amount of dispersant, the agitation rate during the reaction and the concentration of ZOC solution and phosphoric acid. Strong dispersants such as glycerol or tartaric acid in combination with sodium sulfate are preferred.

There was no significant difference in the ammonia adsorption capacity of ZrP products obtained by using various types of additives, but the following observations were made:

(i) Surfactants with more micelle formation (or more foamy surfactants) (e.g. Aerosol 22, sodium lauryl sulfate, Triton 100, Rhodasurf ON-870, Tetronic 1307) tend to increase ammonia adsorption of ZrP slightly even though packing density does not seem to improve.

(ii) The combination of another additive with sodium sulfate helps to improve hardness and packing density of ZrP product, but simultaneously reduces ammonia adsorption capacity slightly unless thermal treatment of the product in water is used to release residual sulfate from ZrP lattice.

For manufacturing purposes, foamy surfactants are less preferred, even though ammonia adsorption may increase slightly. Also, sodium sulfate is still preferred to improve hardness, particle size and packing density of the product. Thus, glycerol/sodium sulfate and tartaric acid/sodium sulfate are preferred in this regard.

No clear improvement was seen in packing density of any particular ZrP product over the others, based on the additive. Additives containing sulfate, carboxylate or glycerol can have higher packing density ZrP than additives containing alcohol, ether, or glycol. Packing density can be also affected by moisture content of the product. Improvement in the packing can be achieved with thermal treatment of product.

Residual surfactants/dispersants may become tightly bound to the ZrP lattice and cannot be effectively removed by washing. If ZrP particles are used in a cartridge for dialysis, and if thermal treatment is not applied to further purify the product, these residual chemicals may be released again during dialysis. For this reason, Triton 100, Rhodasurf ON-870 and 2 amino-2 methyl propanol 95% are not preferred in the formation of ZrP particles that are to be used for dialysis or for any other application in which their release may be a problem, because of their toxicity. On the other hand, ZrP particles made using glycerol/sodium sulfate are more preferred for use in dialysis, according to toxicity testing.

There was no processing difficulty associated with the use of any of the additives in the list. The products do not cause filtration problems during washing or show agglomeration during the reaction and after drying. However, surfactants with more micelle formation (or surfactants that are more foamy) may use excessive washing of the ZrP particles to remove the residual surfactant or foam. Thus, with regard to efficiency, foamy dispersants are less preferred.

Although yield is not likely to be affected by the nature of the additive (the theoretical yield of the sol gel precipitation process should be 100%), there can be a variation of the actual yield associated with the use of different additives, which may be caused by the loss of fine particles during washing and filtration. To avoid possible formation of fragile particles, appropriate additives can be selected for use. From the test results, glycerol, glycerol/sodium sulfate, tartaric acid and sodium lauryl sulfate give better performance than the others.

Based on the above analysis on product quality, process performance, cost and safety factors, the preferred surfactants/dispersants are glycerol, sodium lauryl sulfate, tartaric acid and Aerosol 22. Sodium sulfate may be used in combination with any of the above to enhance crystallinity, hardness, packing density, and particle size uniformity of ZrP.

In the instances wherein a thermal treatment was carried out, ammonia adsorption capacity, particle size uniformity, packing density, and particle hardness were improved. This is believed to be due to the increase of crystallinity and the release of ionic-impurities from the ZrP lattice during the treatment. For example, in the instance wherein the combination glycerol/sodium sulfate was used as an additive, the ZrP product when thermal treatment was not carried out had an ammonium adsorption of about 16.6 mg/gm and packing density of 0.98 gm/cc, whereas the ZrP product when thermal treatment was carried out had an ammonium adsorption of about 17.1 mg/gm and a packing density of 1.05 gm/cc.

Example 10

Scale-up Using Sodium Sulfate and Sodium Lauryl Sulfate (SDS) as Additives

ZrP was synthesized on a pilot scale by the following procedure: A solution of diluted phosphoric acid was made up by mixing 4.52 km of tech grade 76% $H_3PO_4$ with 7 L of deionized or RO water in vessel A. A ZOC solution with SDS and sodium sulfate as additives was made up by first dissolving 100 gm of SDS and 300 gm of sodium sulfate in 2.4 L of deionized or RO water in vessel B and then adding 4 kg of ZOC, in the form of powder crystals, then agitating to form a clear solution of the zirconium polymeric complex. Next, 3 L of the dilute phosphoric acid was transferred from vessel A to a reactor vessel C fitted with an agitator. With a moderately high agitator rate in reactor vessel C, and at room temperature, the ZOC solution was pumped from vessel B into reactor vessel C through a spray nozzle to mix with the phosphoric acid. Sol gel ZrP was formed instantaneously, with the particle size controlled to be in the range of 30-60 microns by the selection of the amount of SDS in the ZOC solution and by selection of the agitation rate. Phosphoric acid lost in the reaction was replenished by pumping in the rest of the phosphoric acid from vessel A. The flow rate of each reactant stream was adjusted so that the addition of both the ZOC solution and the phosphoric acid was completed in approximately 30 minutes, with the completion of the addition of phosphoric acid being slightly ahead of the addition of the ZOC solution.

After the reaction was complete, the product slurry is filtered to remove most of the chloride, excessive phosphoric acid, and additives, including sulfate. The filter cake was transferred to a bath of deionized water (or RO water) and the slurry was agitated for a short time (first wash) at low speed. The filtration and washing were repeated until the TDS level in the slurry was below 1200 ppm.

The filter cake from the last filtration step was transferred to a bath of deionized water (or RO water) in a heating vessel equipped with an agitator. With a moderate agitation speed, the slurry was heated at a moderate rate to about 180-185° F. and the temperature was maintained in this range for about 1 hour. The slurry was then cooled to room temperature and the volume was adjusted with water.

Next, the slurry was titrated with 50% NaOH to bring the pH from about 1.8 to pH 5.75; pH 6; or pH 6.25 to obtain ZrP products of different $Na^+$ contents and acidity. The titrated ZrP was then filtered and washed repeatedly with deionized water (or RO water) until the TDS level in the slurry was below 500 ppm.

The filter cake was transferred after the final wash to a tray dryer and dried to 14-18% LOD at a temperature of about 160°-180° F. The final product was in the form of a free-flowing powder with an average particle size of 30-40 microns, containing less than 1% agglomeration (>100 microns) and less than 10% fine particles (<10 microns). The product had an ammonia adsorption capacity of 16.6 mg/gm and a packing density of 0.8 gm/cc. The yield was 3841 gm. The material was tested in a D-31 cartridge according to a QC single pass test procedure. The particle size can be adjusted by lowering the agitation rate and additive amount. Moreover, it is believed that the packing density can be improved by increasing the time and temperature of the thermal treatment. Furthermore, there were no process difficulties such as agglomeration and gelation during the precipitation reaction, breaking up of particles during the process, filtration difficulty due to formation of fine particles, difficulty to washing ZrP product to achieve a TDS level below 500 ppm or agglomeration of the product upon drying.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method of making zirconium phosphate particles comprising:
    (a) combining at least one fluorine-containing additive with zirconium oxychloride in an aqueous solvent to form a solution wherein the fluorine-containing additive forms a complex with zirconium ions in the solution, and
    (b) combining the solution obtained in (a) with phosphoric acid or a phosphoric acid salt to obtain zirconium phosphate particles by sol gel precipitation.

2. The method of claim 1, wherein the aqueous solvent is deionized water or RO water.

3. The method of claim 1, wherein zirconium oxychloride is dissolved in the aqueous solvent and then the fluorine-containing additive is added to form the solution of step (a).

4. The method of claim 3, wherein the zirconium oxychloride is present in the aqueous solvent at a saturation concentration.

5. The method of claim 1, wherein the fluorine-containing additive is dissolved in the aqueous solvent and then the zirconium oxychloride is added to form the solution of step (a).

6. The method of claim 1, wherein the fluorine-containing additive is present in the solution of step (a) in a molar amount sufficient so that substantially all of the zirconium ions in the solution are converted to a complex.

7. The method of claim 1, wherein the fluorine-containing additive forms a soluble polymer with zirconium ions.

8. The method of claim 1, wherein in step (b), to accomplish the combining of the solution obtained in step (a) with phosphoric acid or phosphoric acid salt, a phosphoric acid solution is titrated to a pH of from about 1 to about 4 and then combined with the solution obtained in step (a).

9. The method of claim 8, wherein the phosphoric acid solution is titrated by adding NaOH to the phosphoric acid solution until a pH of from about 1 to about 4 is obtained.

10. The method of claim 1, wherein in step (b), the solution obtained in step (a) and a solution of phosphoric acid or phosphate are combined so that zirconium ions and phosphate groups are present in a molar ratio of 1 to 3 of zirconium to phosphate.

11. The method of claim 1, wherein in carrying out step (b), the solution of step (a) and the phosphoric acid or phosphate are combined by providing a solution of phosphoric acid in an aqueous solution and adding at least part of the solution of step (a) and at least part of the solution of phosphoric acid simultaneously to a reaction vessel so that the concentration of phosphoric acid is kept constant in the reaction vessel during a period of time that the phosphoric acid is added to the reaction vessel.

12. The method of claim 11, wherein the reaction vessel includes an agitator.

13. The method of claim 1, wherein in carrying out step (b) to obtain the zirconium phosphate particles by sol gel precipitation, a slurry containing at least a zirconium phosphate gel precipitate is formed, and wherein the slurry is agitated.

14. The method of claim 13, wherein the slurry is titrated to a pH of from about 1 to about 2.

15. The method of claim 13, wherein the slurry is titrated to a pH of from about 1 to about 2 by adding NaOH to the slurry.

16. The method of claim 1, further comprising isolating and drying the zirconium phosphate particles obtained in step (b) to obtain a free flowing powder.

17. The method of claim 1, wherein steps (a) to (b) take place at a temperature of from 20° C. to 35° C.

18. The method of claim 1, wherein in step (b), the solution obtained in step (a) is combined with phosphoric acid by providing a reaction vessel and simultaneously adding the solution obtained in step (a) and a diluted solution of phosphoric acid to the reaction vessel.

19. The method of claim 1, wherein steps (a) and (b) take place at ambient temperature, and
    (c) subjecting an aqueous slurry containing zirconium phosphate particles obtained from (b) to a heat treatment above ambient temperature.

20. The method of claim 19, wherein the heat treatment is carried out at a temperature of from about 180 to about 185° F.

21. The method of claim 19, wherein the heat treatment of (c) is carried out for at least one hour.

22. The method of claim 19, wherein the aqueous slurry of (c) is agitated during the heat treatment.

23. The method of claim 19, wherein between (b) and (c), the zirconium phosphate particles obtained in (b) are subjected to washing and filtration before being combined with an aqueous solvent to form the aqueous slurry.

24. The method of claim 19, wherein, after (c), the aqueous slurry is titrated to a pH of about 5.75 and about 6.25.

25. The method of claim 24, wherein the titrated slurry is subjected to washing, filtration, and drying to obtain zirconium phosphate particles as a free-flowing powder.

* * * * *